US008538117B2

(12) United States Patent
Najarian et al.

(10) Patent No.: US 8,538,117 B2
(45) Date of Patent: Sep. 17, 2013

(54) ACCURATE PELVIC FRACTURE DETECTION FOR X-RAY AND CT IMAGES

(75) Inventors: Kayvan Najarian, Glen Allen, VA (US); Simina Vasilache, Annandale, VA (US); Rebecca Smith, Richmond, VA (US); Kevin R. Ward, Glen Allen, VA (US)

(73) Assignee: Virginia Commonwealth University, Richmond, VA (US)

( * ) Notice: Subject to any disclaimer, the term of this patent is extended or adjusted under 35 U.S.C. 154(b) by 36 days.

(21) Appl. No.: 13/255,542

(22) PCT Filed: Mar. 17, 2010

(86) PCT No.: PCT/US2010/027601
§ 371 (c)(1),
(2), (4) Date: Feb. 20, 2012

(87) PCT Pub. No.: WO2010/117575
PCT Pub. Date: Oct. 14, 2010

(65) Prior Publication Data
US 2012/0143037 A1    Jun. 7, 2012

Related U.S. Application Data

(60) Provisional application No. 61/167,279, filed on Apr. 7, 2009, provisional application No. 61/167,275, filed on Apr. 7, 2009.

(51) Int. Cl.
*G06K 9/00* (2006.01)
*A61B 6/00* (2006.01)
*A61B 5/05* (2006.01)

(52) U.S. Cl.
USPC ............................... 382/131; 378/4; 600/407

(58) Field of Classification Search
USPC ............... 382/128, 129, 130, 131, 132, 133, 382/134; 378/4, 8, 21–27, 901; 600/407, 600/410, 411, 425, 427, 433; 128/920, 922
See application file for complete search history.

(56) References Cited

U.S. PATENT DOCUMENTS 6,711,282 B1 * 3/2004 Liu et al. .................... 382/132
8,014,575 B2 * 9/2011 Weiss et al. ................. 382/128
(Continued)

FOREIGN PATENT DOCUMENTS

| JP | 05-260381 | 10/1993 |
|---|---|---|
| JP | 2005-211488 | 8/2005 |
| WO | WO 02-052505 | 7/2002 |

*Primary Examiner* — Abolfazl Tabatabai
(74) *Attorney, Agent, or Firm* — Whitham Curtis Christofferson & Cook, PC

(57) ABSTRACT

Accurate pelvic fracture detection is accomplished with automated X-ray and Computed Tomography (CT) images for diagnosis and recommended therapy. The system combines computational methods to process images from two different modalities, using Active Shape Model (ASM), spline interpolation, active contours, and wavelet transform. By processing both X-ray and CT images, features which may be visible under one modality and not under the other are extracted and validates and confirms information visible in both. The X-ray component uses hierarchical approach based on directed Hough Transform to detect pelvic structures, removing the need for manual initialization. The X-ray component uses cubic spline interpolation to regulate ASM deformation during X-ray image segmentation. Key regions of the pelvis are first segmented and identified, allowing detection methods to be specialized to each structure using anatomical knowledge. The CT processing component is able to distinguish bone from other non-bone objects with similar visual characteristics, such a blood and contrast fluid, permitting detection and quantification of soft tissue hemorrhage. The CT processing component draws attention to slices where irregularities are detected, reducing the time to fully examine a pelvic CT scan. The quantitative measurement of bone displacement and hemorrhage area are used as input for a trauma decision-support system, along with physiological signals, injury details and demographic information.

25 Claims, 12 Drawing Sheets

(56) References Cited

U.S. PATENT DOCUMENTS

| | | |
|---|---|---|
| 2007/0223799 A1 | 9/2007 | Weiss |
| 2008/0292062 A1 | 11/2008 | Marar |
| 2011/0123078 A9 | 5/2011 | Weiss et al. |
| 2012/0020538 A1 | 1/2012 | Weiss |

* cited by examiner

ACCURATE PELVIC FRACTURE DETECTION FOR X-RAY AND CT IMAGES

CROSS-REFERENCE TO RELATED APPLICATIONS

This application is a '371 of international application PCT/US10/27601 filed Mar. 17, 2010 which claims priority to U.S. Provisional Applications Serial No. 61/167,279 filed Apr. 7, 2009 and to Ser. No. 61/167,275 filed Apr. 7, 2009.

STATEMENT OF GOVERNMENT INTEREST

The U.S. Government has a paid-up license in this invention and the right in limited circumstances to require the patent owner to license on reasonable terms as provided for by the terms of Grant No. 05-0033-02 awarded by U.S. Medical Research and Material Command Combat Casualty Care Research Program and by the terms of NSF Grant No. IISO758410.

DESCRIPTION

Background of the Invention

1. Field of the Invention

The present invention generally relates to a system and method for the application of advanced image processing techniques to detect key pelvic structures and, more particularly, to the automated analysis of X-ray radiographs and Computed Tomography (CT) images to provide diagnostic recommendations for physicians and radiologists. As used herein, "X-ray images" refer to plain film radiographs.

2. Background Description

Pelvic fractures are among the most life-threatening injuries that can be suffered by a major trauma patient. Most deaths from such injuries are caused by complications other than the fracture itself; severe hemorrhage is a particularly high risk. Prompt and appropriate treatment is therefore vital to patient survival. X-ray imaging is the first-line diagnostic step in treating pelvic injury patients, due to its speed and low cost. It also causes relatively little disturbance to the injured patient. However, the structure of the pelvis is complex, and fractures may be hard to recognize on low resolution X-rays, even by medical professionals. A system capable of quickly identifying pelvic fracture would prove valuable in a trauma center environment, and a crucial component of such a system is a method to detect and segment key pelvic structures.

Location of fracture has considerable impact on its severity and visual characteristics. Current X-ray segmentation techniques focus on the use of deformable models. However, most studies have focused on segmentation of simpler structures such as bones in the hand. Furthermore, many of these methods rely on some measure of manual interaction by the user to correctly initialize the algorithm, as deformable models are typically very sensitive to initialization in a high stress trauma environment, any useful system would need this to be performed automatically.

Computed Tomography (CT) of the pelvic regions is used to diagnose the more complicated cases, as it is more detailed. CT is usually used to confirm hip displacement, to detect acetabular fracture, to determine whether or not internal bleeding is present and to evaluate the severity of hemorrhage. Identifying and classifying bone by segmenting CT images is an important and challenging task in detecting pelvic fractures. The density of the outer bone—cortical bone—is much higher from that of the core—cancellous bone. Cortical bone appears to be bright and smooth, while cancellous bone is darker and has a sponge-like texture; therefore, bone density cannot be uniformly characterized (see, for example, T. B. S. Authors, H. Tek, J. J. Crisco, and B. B. Kimia, "Segmentation of carpal bones from ct images using skeletally coupled deformable models", *Medical Image Analysis*, 7(1):21-45, March 2003). Differences in density can result in bone not being segmented correctly; regions of bone that need to be connected are identified as being separate. Another factor that adds to the complexity of the problem is the high number of slices in a CT scan. The differences between the positioning of the bones across the slices and the different types of fractures make identifying the presence of a fracture very difficult. Detecting the exact edges of bone is hard as they are diffused due to the partial volume effects in CT images. When distance between distinct bones is small, distinguishing between the bones becomes more difficult.

Pelvic fractures as well as open or closed internal bleeding can be diagnosed by trauma surgeons and radiologists after inspection of X-rays and CT scans of the pelvic region. A system that would analyze these images and identify possible locations of fractures and/or bleeding would be useful in improving the decision-making process.

SUMMARY OF THE INVENTION

An embodiment of the invention provides advanced image processing techniques to analyze pelvic images to detect key pelvic structures for fracture detection.

An embodiment of the invention provides a fully automated system and method to accurately segment bone tissue in order to assess the presence of pelvic fractures.

In an embodiment of the invention, accurate pelvic fracture detection is accomplished with automated X-ray and Computed Tomography (CT) images for diagnosis and recommended therapy. The embodiment combines computational methods to process images from two different modalities. By processing both X-ray and CT images, features which may be visible under one modality and not under the other are extracted and validates and confirms information visible in both. The X-ray component uses hierarchical approach based on directed Hough Transform to detect pelvic structures, removing the need for manual initialization. The X-ray component uses cubic spline interpolation to regulate ASM deformation during X-ray image segmentation. Key regions of the pelvis are first segmented and identified, allowing detection methods to be specialized to each structure using anatomical knowledge. The CT processing component is able to distinguish bone from other non-bone objects with similar visual characteristics, such a blood and contrast fluid, permitting detection and quantification of soft tissue hemorrhage. The CT processing component draws attention to slices where irregularities are detected, reducing the time to fully examine a pelvic CT scan. The quantitative measurement of bone displacement and hemorrhage area are used as input for a trauma decision-support system, along with physiological signals, injury details and demographic information.

According to one aspect of the invention, deformable models are applied to the task of X-ray segmentation, specifically, Active Shape Model (ASM), as has been done previously. However, there are two crucial differences. The first is the use of a hierarchical algorithm to handle automatic initialization based on knowledge of pelvic anatomy This involves the use of Hough Transform and edge detection and some statistical knowledge of bone size and shape. The second is the extension of the standard ASM algorithm to incorporate cubic polynomial splines. These maintain the natural curvature of the pelvic structure and help prevent the model from converging to false edges; a common problem in low resolution X-ray images. Although splines have been used in medical image segmentation before, they have not been combined with ASM and have also not been used primarily for constraining model deformation, as opposed to finding new points on the edge of the desired structure. Both algorithms are trained on a set of images taken from pelvic trauma patients, and tested on a separate set.

According to another aspect of the invention, the system and method employs advanced image processing techniques to analyze pelvic CT images to correctly segment bone tissue in a fully automated manner. The invention implements wavelet processing, Laplacian filtering, morphology operations, a series of region growing techniques and gradient based segmentation methods to create an automated segmentation system and provides an automated decision making system that provides physicians with reliable recommendations for the treatment of traumatic pelvic injuries.

According to a further aspect of the invention, X-ray images and CT images are combined with raw physiological signals and other information, including demographics and injury details, to produce a processed pelvic trauma database. Machine learning methods are applied to this database in a trauma decision-support system. More particularly, machine learning techniques, including creating decision trees and extracting rules, are applied to the database to generate predictive models of patient outcome. These models are used to provide recommendations and predictions to physicians, assisting them in making rapid and accurate treatment choices for new patients.

While the invention is described in terms of a specific embodiment specialized toward pelvic injuries, those skilled in the art will recognize that the techniques implemented by the embodiment can be adapted to other bone structures, and the analysis methods reconfigured using anatomical knowledge.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

The embodiment of the invention is described in terms of a system on which the methods of the invention may be implemented. The system is composed of various imaging components, databases and computational interfaces that one of ordinary skill in the computational arts will be familiar with. The methods of the invention are described with reference to flowcharts which illustrate the logic of the processes implemented. The flowcharts and the accompanying descriptions are sufficient for one of ordinary skill in the computer programming and image processing arts to prepare the necessary code to implement the embodiment of the invention.

Figure 1:
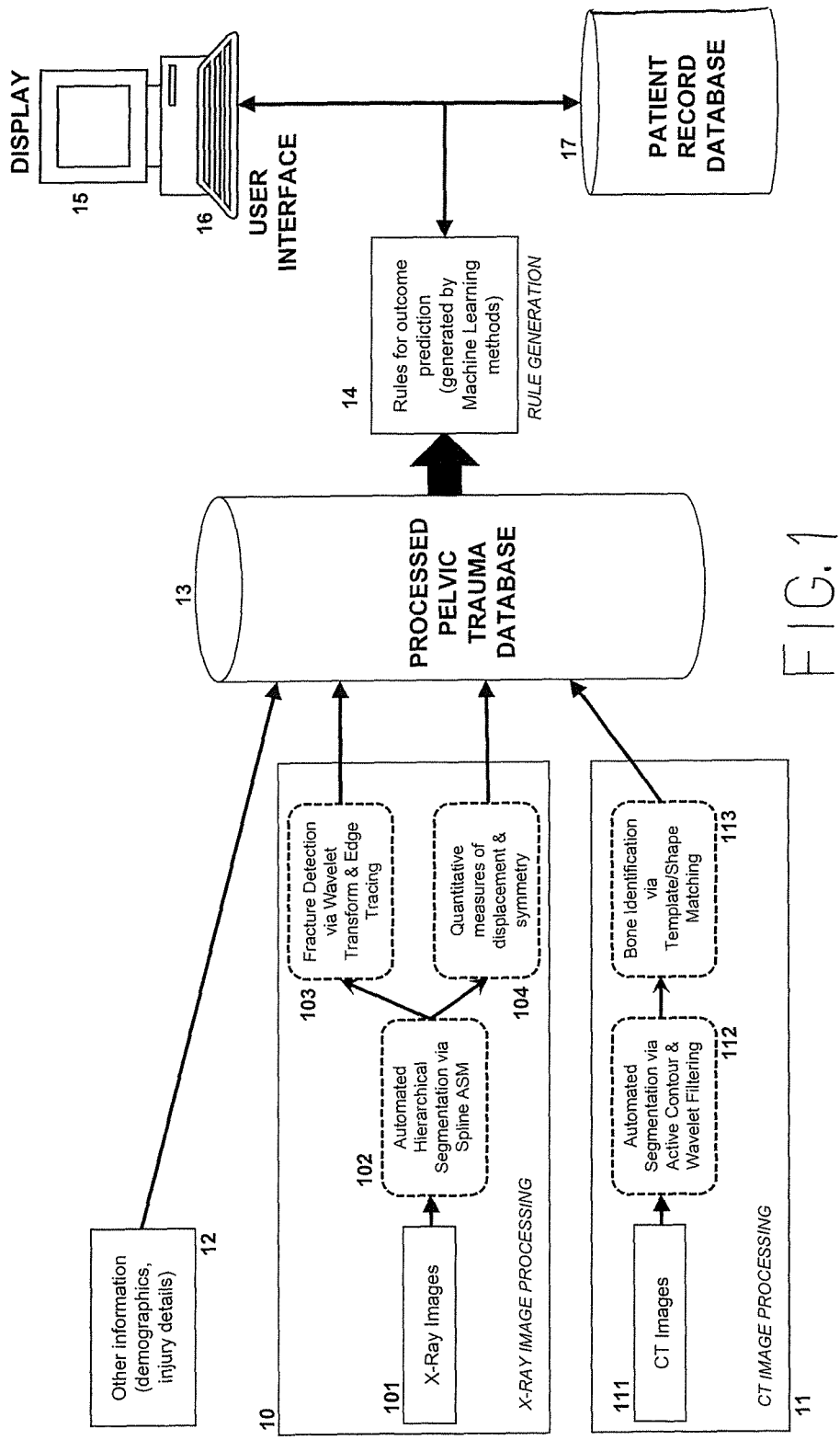
FIG. 1 is a block diagram illustrating an embodiment of the decision support system according to the invention.

Referring now to the drawings, and more particularly to FIG. 1, there is presented in block diagram form an overview of the decision support system framework, and the function that the X-ray and CT components serve. X-ray image processing is performed at 10, the X-ray images being input at 101. CT image processing is performed at 11, the CT images being input at 111. Other information, including demographics, injury details, etc., are input at 12. The X-ray images input at 101 are subjected to automated hierarchical segmentation via spline Active Shape Modeling (ASM) at 102. Then, fracture detection via wavelet transform and edge tracing is performed at 103. Additionally, quantitative measures of displacement and symmetry are performed at 104. CT images input at 111 are subjected to automated segmentation via active contour and wavelet filtering at 112. Then, bone identification via template/shape matching is performed at 113. The data from 12, 103, 104, and 113 are input to a processed pelvic trauma database 13. The processing done thus far may be referred to as pre-processing, and the data stored in database 13 is pre-processed data, requiring further processing in order to generate diagnosis and recommended therapy.

This database 13 is accessed by data processor 14 which applies machine leaning techniques, specifically creating decision trees and extracting rules, to generate predictive models of patient outcome. In the training phase, the demographic and injury data input at 12 and stored in database 13 is a prior dataset used to train the predictive model generated by the data processor 14. This prior dataset, in the case of the embodiment of the invention, was obtained from two hospitals, along with matching CT and/or X-ray images for each patient and their eventual outcome. When the generated model is later used to make predictions for a new patient, the same information is collected and used as input. These models are used by the system to provide recommendations and predictions to physicians, assisting them in making rapid and accurate treatment choices for patients. The recommendations and predictions are displayed on display 15, and data processor 14 correlates the recommendations and predictions and actions taken by the physician, as input on user interface 16, with the patient's records, which are stored in patient record database 17.

Figure 2:
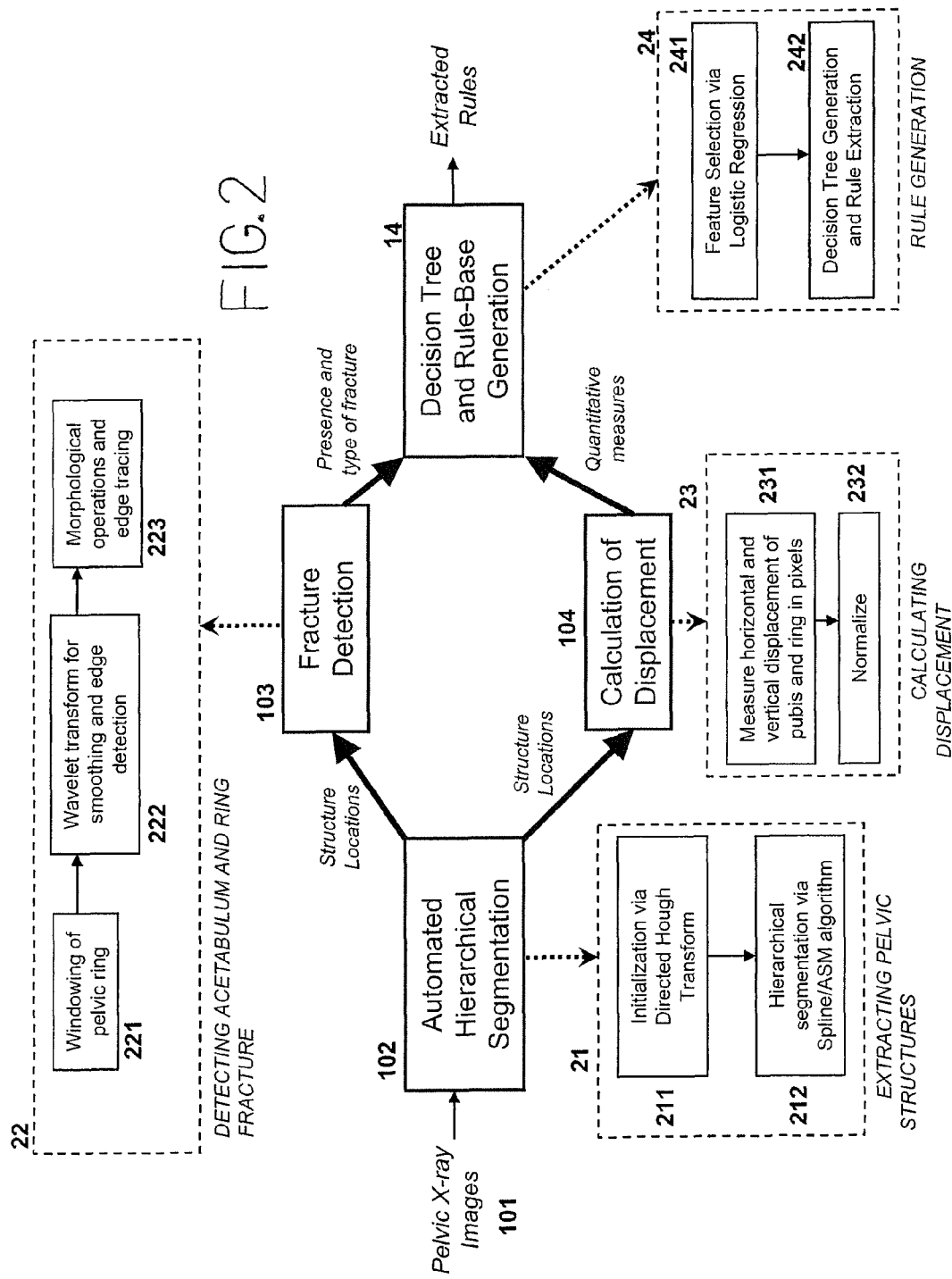
FIG. 2 is a flowchart providing an overview of the logical processes implemented by the X-ray fracture detection component of the embodiment shown in FIG. 1.

FIG. 2 presents a flowchart describing the operation of the X-ray fracture detection subsystem. The pelvic X-ray images 101 are input to the process of automated hierarchical segmentation 102. This process is performed as generally illustrated by process 21 and described in more detail with reference to FIG. 3. Process 21 includes the process 211 of initialization via directed Hough Transform followed by process 212 of hierarchical segmentation via spline/ASM algorithm. The output of process 102 is structure locations which are input to the fracture detection process 103 and the calculation detection process 104. The fracture detection process 103 is performed as generally illustrated by process 22, which is the detection of acetabuilum and ring fracture process. This process is described in more detail with reference to FIG. 5. Briefly described here, the first step 221 is windowing of the pelvic ring. The next step 222 is wavelet transform for smoothing and edge detection. Then, in step 223, morphological operations and edge tracing are performed. The calculation of displacement process 104 is performed as generally illustrated by process 23, and described in more detail with reference to FIG. 4. The first step 231 is to measure the horizontal and vertical displacement of pubis and ring in pixels. The next step 232 is to normalize the calculation. The output of the fracture detection process 103 is an indication of the presence and type of fracture. The output of the calculation of displacement process 104 are quantitative measures. These outputs are input to the pelvic trauma database 13 shown in FIG. 1. Subsequently, this data is accessed by the data processor 14 which implements the decision tree and rule-base generation process. As will be described in more detail with reference to FIG. 10, rule generation is performed as generally indicated in process 24. This process has as a first step 241 feature selection via logistic regression. Then, in step 242, decision tree generation and rule extraction is performed. The output of the decision tree and rule-base generation process is extracted rules.

Figure 3:
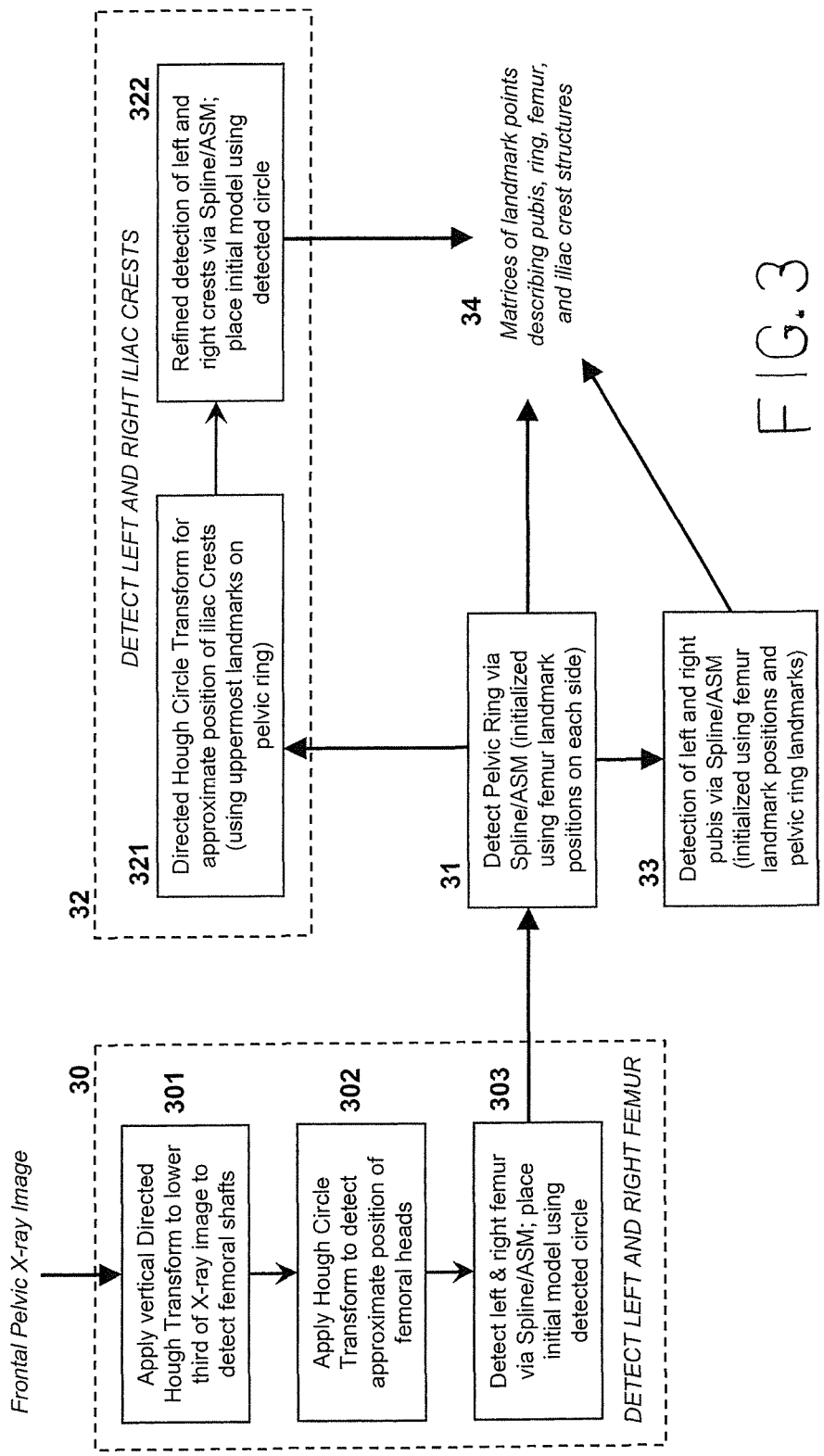
FIG. 3 is a flowchart illustrating the logical process which implements the automated hierarchical segmentation component of the X-ray fracture detection component shown in FIG. 2.

The process of hierarchical automated segmentation of pelvic structures, illustrated generally at 21 in FIG. 2, is shown in more detail in FIG. 3. This component requires training prior to deployment. This only needs to be done once, using a set of training X-ray images where the specific structures to be detected have been labeled (by placing landmark points around their edges). This component of the system segments key structures from an input frontal pelvic X-ray, supplied as a Digital Imaging and Communications in Medicine (DICOM) file. With reference to FIG. 3, a frontal pelvis X-ray image of pelvic trauma patient is input to process 30. At step 301, vertical Directed Hough Transform is applied to the lower third of X-ray image to detect femoral shafts. The Directed Hough transform examines each pixel in the given image portion and looks for evidence of a straight line restricted to ±45° of the vertical. If one is found, the transform calculates the unknown parameters m and b of the straight line equation y=mx+b. The process then increases the value of the corresponding bins for m and b in a two dimensional (2D) accumulator array. After all pixels are considered, a set of candidate femoral shaft edges are extracted by finding the bins with the highest values via thresholding. These are then paired into candidate shafts.

The probability $p_i$ that a pair of lines i in the test image form a shaft contour is given by:

$$P_i \propto M_i G_\omega(\omega_i | \mu_s, \sigma_s) \quad (1)$$

where $\mu$ and $\sigma$ are the mean and standard deviation of shaft width calculated from a sample training set of X-ray images and $M_i$ is the mean of the intensity gradient magnitudes of the points along both lines in the pair. The top four candidates are kept. A similar process is then used to match shaft pairs, using a distribution calculated based on the distance between the left and right shafts in the X-ray training set. Full implementation details of Hough Transform for line and circle detection can be found "Use of the Hough Transformation to Detect Lines and Curves in Pictures" (Richard O. Duda and Peter E. Hart, Technical Note 36, Artificial Intelligence Center, 1971).

In step 302, Hough Circle Transform is applied to detect approximate position of femoral heads. The process of step 301 returns coordinates representing detected femoral shaft edges. These are used to direct Hough Transform circle detection to identify the femoral heads on both sides. This uses the same approach as Hough Line Transform in Box 1, except it uses a three dimensional (3D) accumulator since there are three unknown parameters a, b, and r (for the parametric circle equation $(x-a)^2+(y-b)^2=r^2$).

In step 303, the left and right femur are detected via Spline/ASM; place initial model using detected circle. On each side, the topmost point on the detected femoral head circle is used to initialize Spline/ASM to detect the femur as a whole. This component combines cubic spline interpolation with the standard Active Shape Model (ASM) deformable model approach.

Standard ASM searches for a target shape in an image using a model defined by an set of landmark points. It takes as input a series of training images in which the target shape has been labeled by landmark points. These images provide a set of shapes represented as vectors of (x, y) coordinates. Alignment and Principal Component Analysis are performed on the set, so each shape can be approximated by $$x \approx \bar{x} + Pb \quad (2)$$

where P contains the t eigenvectors of the covariance matrix calculated during PCA, and b is a t-dimensional vector which defines the parameters for the deformable shape model. A grey-level model is built by sampling the derivative of the intensity values along the profile normal to the landmark in each training image. For each landmark, the normalized mean $\bar{g}$ and covariance $S_g$ of the sample is calculated. During each iteration of the shape matching process, a specific number of pixels are sampled along the profile normal to each current landmark point $p_i$. The quality of fit for each pixel $q_i=(x_q, y_q)$ is calculated as:

$$f(g_s) = (g_s - \bar{g})^T S_g^{-1} (g_s - \bar{g}) \quad (3)$$

The landmark point is moved to the pixel with the lowest value of $f(g_s)$ and b is updated to fit these new positions. The process halts when an iteration results in no significant changes in b. More details of basic ASM are found in "Active shape models—their training and application" (T. F. Cootes, C. J. Taylor, D. H. Cooper, and J. Graham, Computer Vision and Image Understanding, vol. 61, no. 1, pp. 38-59, January 1995).

Spline/ASM incorporates cubic spline interpolation into the ASM quality of fit function. Cubic spline interpolation is used to approximate more complicated curves, and involves building a cubic spline from n piecewise cubic polynomials between a set of given data points along the curve. Given n+1 distinct knots (points) $x_i$ where I=0, . . . , n and n+1 corresponding knot values $y_i$, the aim is to find a piecewise cubic spline function S(x) such that $$S(x) = \begin{cases} s_1(x) & \text{if } x_1 \leq x < x_2 \\ s_2(x) & \text{if } x_2 \leq x < x_3 \\ \ldots \\ s_{n-1}(x) & \text{if } x_{n-1} \leq x < x_n \end{cases} \quad (4)$$

where $s_i$ is a polynomial of degree three given by:

$$s_i(x) = a_i(x-x_i)^3 + b_i(x-x_i)^2 + c_i(x-x_i) + d_i \quad (5)$$

for I=1, 2, . . . , n−1. These polynomials can be used to construct a tridiagonal system of equations and solved using the tridiagonal matrix algorithm (TDMA) to find the unknown coefficients.

In Spline/ASM, when considering landmark point $p_j$, an interpolated cubic spline function is constructed using m points on each side of $p_j$. This function is used to predict the best new location of point $p_j$ using its x-coordinate, to give the predicted point location $l_p = (x_l, y_l)$. When considering pixel $q_i$, as a possibly new landmark location, the distance between $q_i$ and $l_p$, is calculated and squared to obtain an error measure e:

$$e = abs(x_q - x_l) + abs(y_q - y_l) \quad (6)$$

The quality of fit function then becomes:

$$f(g_s) = (g_s - \bar{g})^T S_g^{-1}(g_s - \bar{g}) + \alpha^* e \quad (7)$$

where α is chosen via experimental results. In the most recent set of experiments, the optimal value of α was found to be 0.00001.

Spline/ASM requires initial placement of the shape model, which will then try to deform to the nearest suitable edges. For the femur, this placement is done by matching the position of the topmost landmark on the femur shape model with the topmost point of the femoral head circle detected in process step 302.

Process step 303 passes on two matrices describing the detected left and right femurs. Each matrix consists of multiple coordinate pairs: sequential points in the image that define the femur. Two selected coordinate pairs, one from the left femur and one from the right femur, are used to initialize placement of the pelvic ring model. Spline/ASM is then repeated to detect the pelvic ring in process 31.

The output of process 31 is input to process 32 to detect left and right iliac crests. In step 321, directed Hough Circle Transform is used for approximate position of iliac Crests (using uppermost land-marks on pelvic ring). The two uppermost landmark points on the pelvic ring are used to create two separate windows likely to contain the left and right iliac crests. These windows are used to direct Hough Circle Transform for approximate detection of the crests. In step 322, refined detection of left and right crests is performed via Spline/ASM. For each crest, the topmost point on the circle detected in step 321 is used to initialize placement of the iliac crest ASM model. Spline/ASM is then performed to detect the crest.

The process in step 33 detects left and right pubis via Spline/ASM (initialized using femur landmark positions and pelvic ring landmarks from step 31). For each side of the pubis, two selected coordinate pairs—one from the femur and one from the pelvic ring—are used to initialize placement of the pubis ASM model. Spline/ASM is then performed to detect each side of the pubis.

The output 34 of this stage is a set of detected pelvic structures, i.e., iliac crests, pelvic ring, pubis, and femurs, in the form of matrices of landmark points around the edge of each structure.

Figure 4:
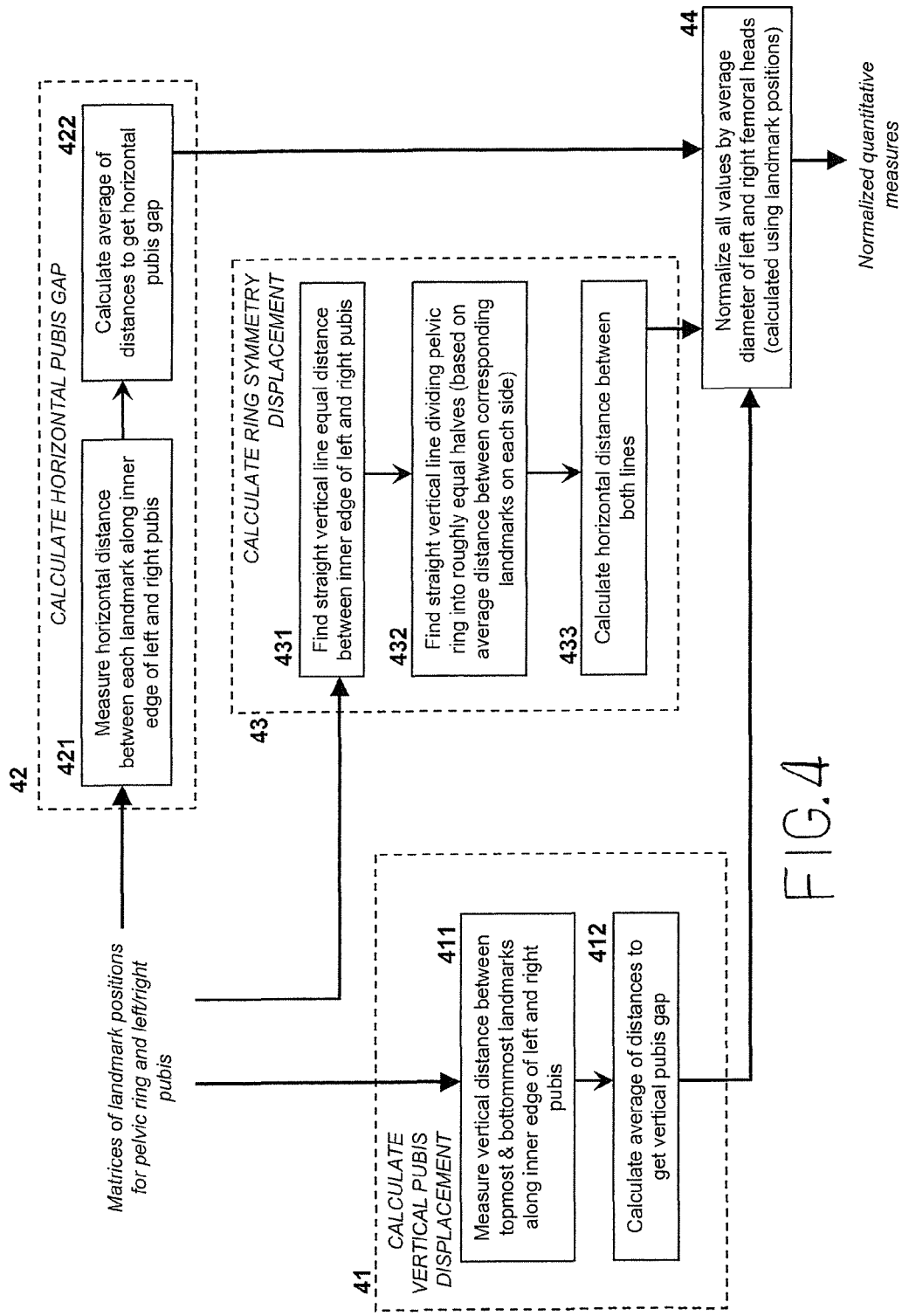
FIG. 4 is a flow chart illustrating the logical process implementing the calculation of displacement and symmetry measures component of the X-ray fracture detection component shown in FIG. 2.

The calculation of displacement process 23 shown in FIG. 2 is illustrated in more detail in FIG. 4. This stage of the system calculates displacement and symmetry measures using the structures segmented in the first stage 102. A set of pelvic structures detected in stage 102, iliac crests, pelvic ring, pubis, and femurs, in the form of matrices of landmark points around the edge each structure are input. Process 41 calculates vertical pubis displacement. At step 411, the vertical distance between topmost and bottommost landmarks along inner edge of left and right pubis is measured, and then in step 412, the average is calculated to get vertical pubis displacement. Each detected side of the pubis is represented by a matrix of (x, y) points. On each side, the topmost and bottommost points on the inside vertical edge of the pubis are selected to give two pairs of points: $t_l = (x_{tl}, y_{tl})$, $t_r = (x_{tr}, y_{tr})$, $b_l = (x_{bl}, y_{bl})$, $b_r = (x_{br}, y_{br})$. Vertical displacement is calculated as:

$$\frac{1}{abs(y_{tl} - y_{tr}) + abs(y_{bl} - y_{br})} \quad (8)$$

The structures segmented in the first stage 102 are also input to process 42 for calculation of the horizontal pubis gap. In step 421, the horizontal distance between each landmark along inner edge of left and right pubis is measured, and in step 422, the average of distances is calculated to get horizontal pubis gap. Horizontal gap is determined by calculating the average horizontal distance between the left and right pubis. The n landmarks along the inside edges of each structure's model are paired up, and the difference in the x-coordinates of each pair is calculated and the results averaged over the number of landmarks n. Let $(lx_i, ly_i)$ be the landmark coordinates on the left pubis and $(rx_i, ry_i)$ those on the right pubis, where I=0, . . . , (n−1). The horizontal gap g is calculated as:

$$g = \frac{1}{n}\sum_{i=0}^{n-1}|x_i - x_j| \quad (9)$$

The structures segmented in the first stage 102 are also input to process 43 to calculate ring symmetry displacement. In step 431, a straight vertical line equal distance between inner edge of left and right pubis is found. This step finds the vertical straight line roughly equal distance between the left and right pubis. The line is found using the calculations already completed in steps 421 and 422. In step 432, a straight vertical line dividing pelvic ring into roughly equal halves is found (based on average distance between corresponding landmarks on each side). By comparing the line calculated in step 431 to a second line dividing the area inside the pelvic ring into two roughly symmetric halves, symmetric displacement can be measured (which may indicate deformation of the pelvic structure and loss of ring integrity). This second line is calculated in a similar method to the horizontal gap in steps 421 and 422, using corresponding landmarks on either side of the pelvic ring model in place of those on the inside edge of the pubis. Then in step 433, the horizontal distance between both lines is calculated. The horizontal distance between the vertical straight lines constructed in steps 431 and 432 is calculated as the absolute difference of their x-coordinates.

Process 44 receives the outputs from each of processes 41, 42 and 43 and normalizes all values by average diameter of left and right femoral heads (calculated using landmark positions). The distance of the X-ray machine from the patient may vary; therefore, the pelvic structure size will not be standardized across multiple X-ray images. To adjust for this, the raw displacement and symmetry measures are normalized using the average diameter in pixels of the left and right femoral heads.

Figure 5:
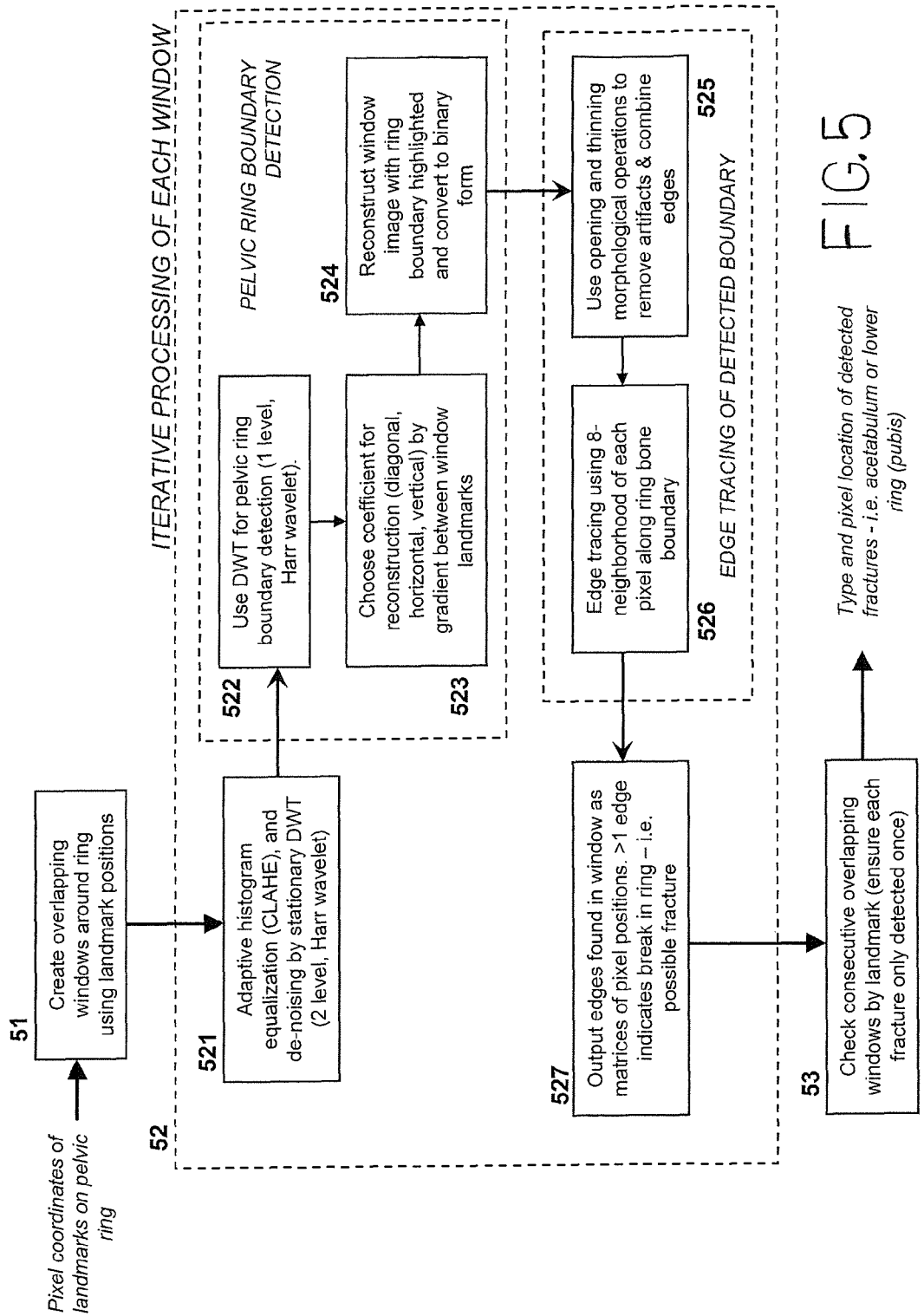
FIG. 5 is a flowchart illustrating the logical process implementing the fracture detection component shown in FIG. 2.

The fracture detection process 103 shown in FIG. 2 is illustrated in more detail in FIG. 5. This stage of the system detects fractures of the acetabulum, upper pubis and general pelvic ring using the structures segmented in the first stage. The input to this stage is the set of pelvic structures detected in stage 102, i.e., iliac crests, pelvic ring, pubis, and femurs, in the form of matrices of landmark points around the edge each structure. In step 51, overlapping windows are created around the pelvic ring using landmark positions. The pelvic ring is represented by twenty-six consecutive landmarks, starting at the top right and ending at the top left. This structure is separated into overlapping windows, each covering four landmarks, and each window is analyzed separately for presence of fracture. The windows overlap, i.e., the first window covers landmarks one to four, the second window covers landmarks three to seven, etc., to prevent fractures crossing between windows from being missed. Each window is labeled according to the type of fracture it is likely to contain; here, acetabulum, upper pubis, or general pelvic ring.

The output window of step 51 is subject iterative processing in process 52. In step 521, adaptive histogram equalization and de-noising by DWT (2 level, Haar wavelet) is performed. Step 51 outputs a set of window sub-images around the ring. Each is analyzed individually. X-rays are often low-contrast, therefore Contrast Limited Adaptive Histogram Equalization (CLAHE) is first performed on the window to make the ring edges more visible. CLAHE partitions the X-ray into regions and applies histogram equalization to CLAHE one, improving contrast and evening out grey-level distribution. This is widely used in imaging software and the full mathematical details of the algorithm can be found in "Contrast Limited Adaptive Histogram Equalization" (Karel Zuiderveld, Academic Press Graphics Gems Series, Graphics Gems IV, pp. 474-485 1994). The window is then de-noised via two-level 2D stationary wavelet decomposition using the Haar wavelet. This decomposes the window into two levels of approximation and detail coefficients. The detail coefficients are thresholded. All coefficients are used to reconstruct the window, which is now de-noised. This simplifies edge detection by smoothing over X-ray artifacts; stationary wavelet decomposition is used as it does not require sub-sampling of the original window. The mathematical description of SWT is lengthy; it can be found in full in "The Stationary Wavelet Transform and some Statistical Applications" (G. P. Nason and B. W. Silverman, Dept. of Mathematics, University of Bristol, 1995).

In step 522, a 2D Discrete Wavelet Transform (DWT) is used for pelvic ring boundary detection (1 level, Haar wavelet). Single-level 2D wavelet decomposition is performed on the de-noised window using the Barr wavelet. The window is regarded as a series of one dimensional (1D) row signals and as a series of 1D column signals. The 1D DWT is calculated for each row, and the N rows of result values used to form a matrix $X_v$. The same is repeated for columns to form a matrix $X_h$. This process is repeated on $X_v$ and $X_h$, giving output matrices $X_{hh}$, $X_{vv}$, $X_{hv}$, and $X_{vh}$. The first two contain information on the window's vertical and horizontal variations, respectively, and the third and fourth the diagonal variations (the detail coefficients for the window). More information on 2D DWT can be found in *Biomedical Signal and Image Processing* (Kayvan Najarian and Robert Splinter, CRC Press, 2006).

In step 523, the coefficient for reconstruction is chosen (diagonal, horizontal, vertical) by gradient between window landmarks. The best detail coefficient for edge detection is chosen as the one most similar in direction and angle to the bone boundary. The gradient of the bone boundary is approximated by the gradient along the landmark points used to select the window. If the absolute value of the gradient is closest to 0, the horizontal coefficient is chosen; 0.5, the diagonal; 1, the vertical.

In step 524, the window image is reconstructed with ring boundary highlighted and converted to binary form, and then, in step 525, opening and thinning morphological operations are used to remove artifacts and combine edges. The chosen coefficient at level one decomposition is used to reconstruct the window. The resulting 8-bit grey-level image is thresholded to create a binary image. The threshold value is chosen using Otsu's method, such that it minimizes the intra-class variance of the black and white pixels. Implementation details are in "A Threshold Selection Method from Grey-Level Histograms" (Nobuyuki Otsu, *IEEE Trans. on Systems, Man and Cybernetics*, vol. SMC-9, No. 1, January 1979). The resulting binary image will highlight the boundary detected by the wavelet transform in white pixels. However, there will be noise, such as dual edges and isolated pixels or small objects. A sequence of morphological opening and thinning operations is performed to remove these pixels and artifacts, and join close edges along the detected bone boundary.

In step 526, edge tracing using 8-neighborhood of each pixel along ring bone boundary is performed. After steps 524 and 525, the output is a binary image in which the approximate bone boundary appears as a white line. If there are fractures present, this line will have breaks. Starting at the top of the window, the edge is traced using 8-neighbor connectivity. If the end of the edge is reached, i.e., there are no more white pixels, a new edge is started.

In step 527, the edges found in window are output as matrices of pixel positions. >1 edge indicates break in ring, i.e., a possible fracture. If more than one edge is returned from 526, there is a possible fracture. The edges are stored as matrices of pixel positions; therefore, the end pixels of the two edges either side of the break can be used to identify the potential fracture's location. This is originally given in coordinates relative to the window, and is therefore adjusted based on window position to give coordinates relative to the entire X-ray image.

In step 53, consecutive overlapping windows are checked by landmark (ensure each fracture only detected once). Each window covers four landmarks, with the final two overlapping with the start of the next window. The windows are considered in sequence; if a detected fracture falls within these two landmarks, it will not be counted in the following windows. Fracture type, e.g., acetabulum, upper pubis, or general pelvic ring, is identified by window label, as described in step 51.

Figure 6:
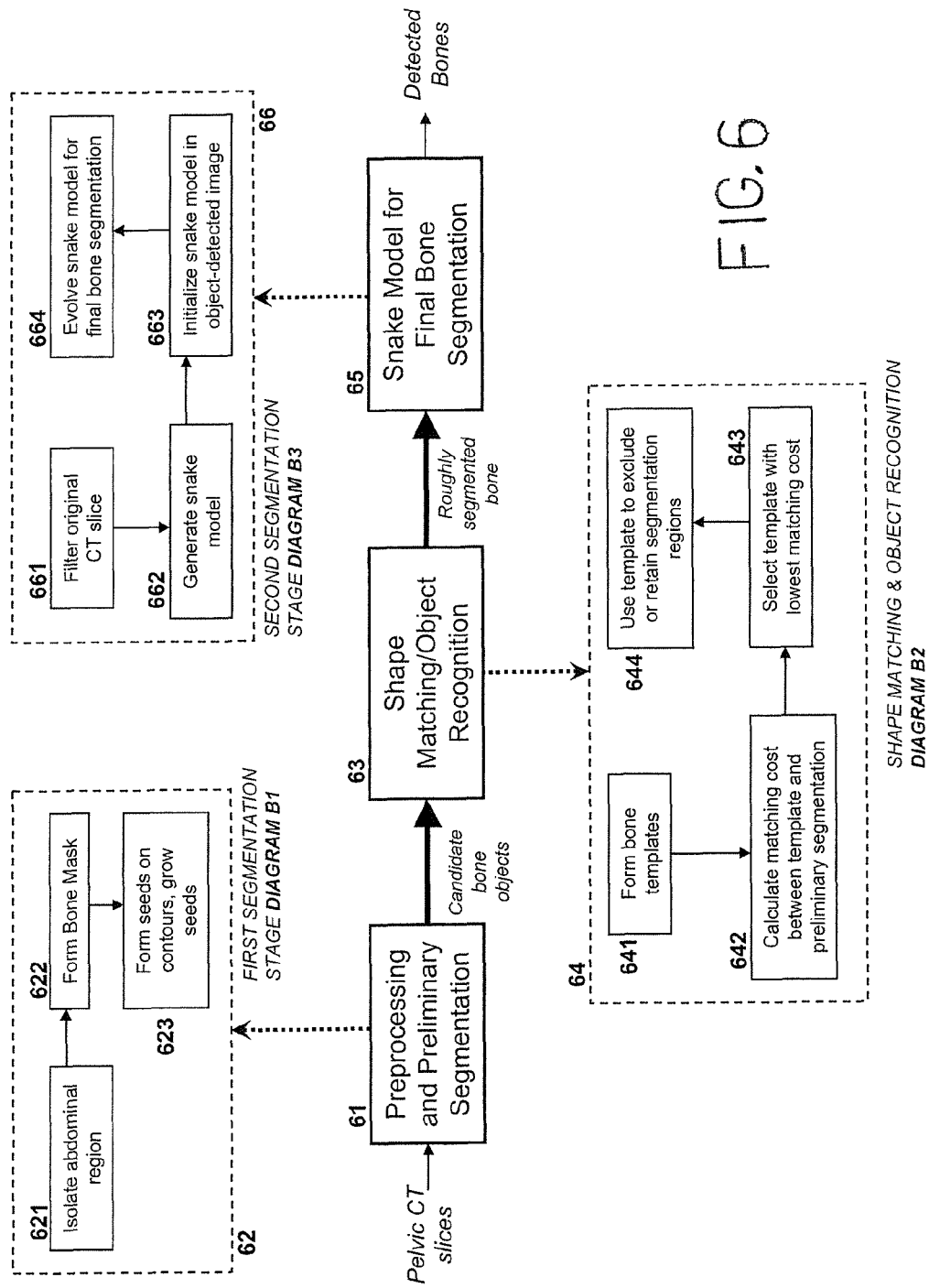
FIG. 6 is a flowchart illustrating the logical process implementing the CT bone detection component of the embodiment shown in FIG. 1.

Turning next to the CT image processing system 11 in FIG. 1, reference is now made to FIG. 6 which presents a flowchart describing the operation of the CT bone detection subsystem. Pelvic CT slices are input at 111 to a process 61 which performs preprocessing and preliminary segmentation. This is accomplished by the process generally indicated at 62, the first segmentation stage, and described in more detail with reference to FIG. 7. The first step 621 of this process is to isolate the abdominal region. Next, in step 622, the bone mask is formed. Then, in step 623, seeds are formed on the contours and the seeds are grown. The output of process 61 are candidate bone objects. These are received by process 63, shape matching/object recognition. This is accomplished by the process generally indicated at 64 and described in more detail with reference to FIG. 8. The first step 641 is to form bone templates. Then, matching cost between template and preliminary segmentation is calculated at step 642. Based on this calculation, the template with the lowest matching cost is selected at step 643. The selected template is used in step 644 to exclude or retain segmentation regions. The output of the shape matching/object recognition process 63 is the roughly segmented bone. This is input to the snake model for final bone segmentation process 65. This is accomplished by the process indicated at 66, second segmentation stage. The first step 661 is to filter the original CT slice. Then, in step 662, a snake model is generated. This is input to step 663 which initializes the snake model in the object-detected image. Finally, in step 664, the snake model is evolved for final bone segmentation. The output is the detected bones.

Figure 7:
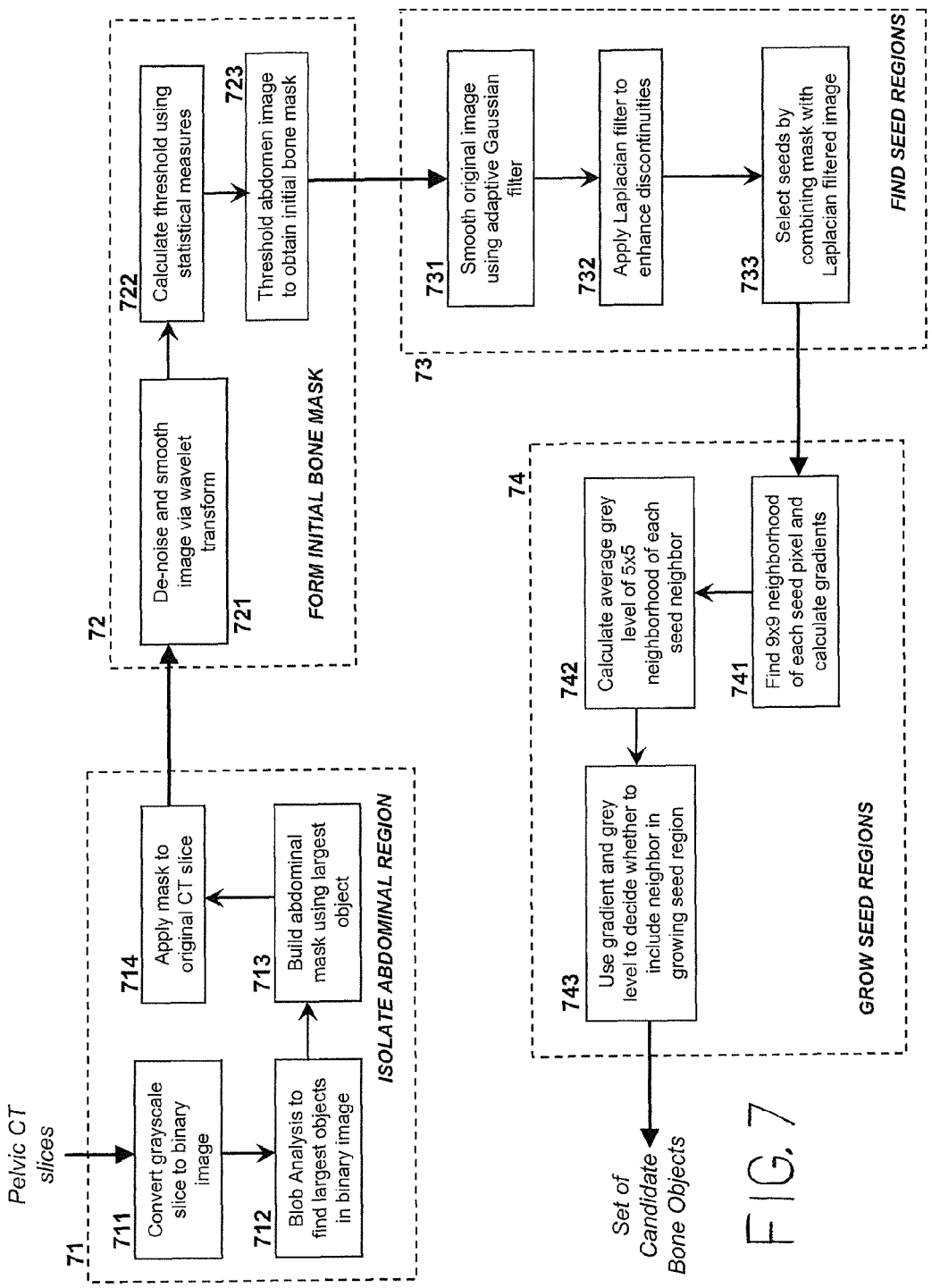
FIG. 7 is a flowchart illustrating the logical process implementing the first CT segmentation component shown in FIG. 6.

The first segmentation stage 62 is shown in more detail in FIG. 7. This stage of the. system performs initial segmentation of a single CT slice, removing artifacts and returning a set of regions that may contain bone matter (candidate bone objects). The input to this stage is an individual pelvic CT slice.

The first process 71 isolates the abdominal region. At step 711, the CT slice is converted to binary image, and in step 712, blob analysis is used to find the largest object. Since bone matter has a brighter grey-level value than soft tissue, the slice is thresholded to a binary (black and white image). As with steps 524 and 525 in FIG. 5, Otsu's method is used to determine the most appropriate threshold. Bright objects in the slice will appear as white pixel regions in the binary image. Since binary thresholding is always approximate, morphological operations such as opening are applied to disconnect these objects. For example, cables around the patient often appear as bright pixel regions in the CT slices, and must be disconnected from the main abdominal region. Since the abdominal area will always be the largest object in a CT slice, blob analysis is used in step 712 to calculate the area of each detected object, and the largest one is retained.

In step 713, an abdominal mask is built using largest object. The abdominal object detected in step 712 is isolated into a new binary image: the abdominal mask. This mask is multiplied in step 714 with the original CT slice to isolate the abdominal area from background artifacts. The resulting image will be known as $I_2$.

The image $I_2$ is input to process 72 to form the initial bone mask. In step 721, the image de-noised and smoothed via Gaussian filter and wavelet transform. A 2D Gaussian filter is applied to image $I_2$ to reduce noise. This is the product of two 1D Gaussian filters, and is formulated as:

$$G(x, y) = \frac{1}{2\pi\sigma^2} e^{-\frac{x^2+y^2}{2\sigma^2}} \quad (10)$$

where x and y are the distances from the original on the horizontal and vertical axes, respectively, and $\sigma$ is the standard deviation of the Gaussian. Wavelet analysis is then performed on the Gaussian filtered image (known as $I_3$) to highlight edges. This is done via 2D Discrete Wavelet Transform (DWT) with Haar wavelet; the output image is reconstructed using the approximation coefficients. The wavelet filtered image $I_4$ is given by:

$$I_4 = T I_3 T^{-T} \quad (11)$$

where $$T = \frac{1}{\sqrt{2}} \begin{bmatrix} 1 & 1 \\ 1 & -1 \end{bmatrix}.$$

In steps 722 and 723, the threshold is calculated using statistical measures and threshold bone mask. First, we calculate the mean and standard deviation of the grey-level values of all pixels in $I_4$. These are used to calculate the threshold $t_1$ for creating a bone mask, given by $t_1 = m_1 + st_1$, where:

$$m_1 = \frac{\sum_{x=0}^{N-1} \sum_{y=0}^{M-1} f(x, y)}{NM - Card(S)} \quad (12)$$

$$st_1 = \sqrt{\frac{\sum_{x=0}^{N-1} \sum_{y=0}^{M-1} (f(x, y) - m_1)^2}{NM - Card(S)}} \quad (13)$$

and $$S = (x, y) \mid f(x, y) = 0 \quad (14)$$

In this case, S is the set of the background pixels with zero grey-level value, and Card(S) is its cardinality. This threshold is applied to image $I_3$ to obtain a initial bone mask $B_1$.

The initial bone mask output from process 72 is input to process 73 to find seed regions. At step 731, the original image smoothed (i.e., eliminate noise from original image) using adaptive Gaussian filter. The initial bone mask $B_1$ returned from step 723 is refined to create an intermediary bone mask $B_2$. First, an initial Gaussian filter is applied to the abdominal image $I_2$ to create filtered image $G_1$. The difference image $D_1$ is formed by subtracting $G_1$ from $I_2$. The standard deviation $\sigma$ of the grey-level values of $D_1$ is then calculated, and used to determine the size of a filter window to be used in constructing an adaptive Gaussian filter, which offers better noise reduction. Full details are found in "An Adaptive Gaussian Filter For Noise Reduction and Edge Detection" (G. Deng and L. W. Cahill, Nuclear Science Symposium and Medical Imaging, 1994). The adaptative 2D Gaussian filter is applied to $I_2$, creating image $I_5$. The initial bone mask $B_1$ is applied to this image via multiplication to create the intermediary bone mask $B_2$.

In step 732, Laplacian filter is applied to enhance discontinuities, and then in step 733, Canny edge detection is performed to find seed regions. A Laplacian filter is applied to the original image $I_2$ for edge detection. Seeds scattered in the brightest regions of the slice are then identified by selecting the pixels in the filled mask $B_2$ with corresponding negative values in the Laplacian filtered image. The regions containing these seeds are then identified using Canny edge detection, as outlined in "A Computational Approach to Edge Detection" (Canny, 1986). The edge pixels and seed pixels for each region are combined, and regions less than 50 pixels in area are discarded. Contour seeds are placed on the edges of the remaining regions (again detected using the Canny method).

The output of process 73 is input to process 74, growing seed regions. At step 741, 9×9 neighborhood of each seed pixel is found and gradients calculated. Each seed placed in steps 723 and 731 is considered in turn. The 9×9 pixel neighborhood of each seed pixel is found; i.e., a set of the 80 pixels forming a 9×9 square around the seed pixel in the image (excluding the seed pixel itself). The gradients of the grey-level values between the seed pixel and each of its neighbor are then calculated. After all gradients are calculated, the average gradient $v_a$ is found.

At step 742, average grey-level of 5×5 neighborhood of each seed neighbor is calculated. For each neighbor pixel found in step 741, we extract its 5×5 neighborhood. This contains 24 pixels in total. We calculate the average grey-level value $g_a$ of all 24 pixels.

Finally in step 743, the gradient and grey-level is used to decide whether to include neighbor in growing seed region. The neighbor is added to the seed set if it is on the inside of the edge; its grey-level value is $\geq g_a$ as calculated in step 743, and the gradient value between the seed and the neighbor calculated in 742 is $v_a$. Note that steps 741 to 743, the region growing stage, are repeated until either until ten iterations have occurred, or until the number of new seeds that an iteration adds is less than 10% of the number of existing seeds in the region.

Figure 8:
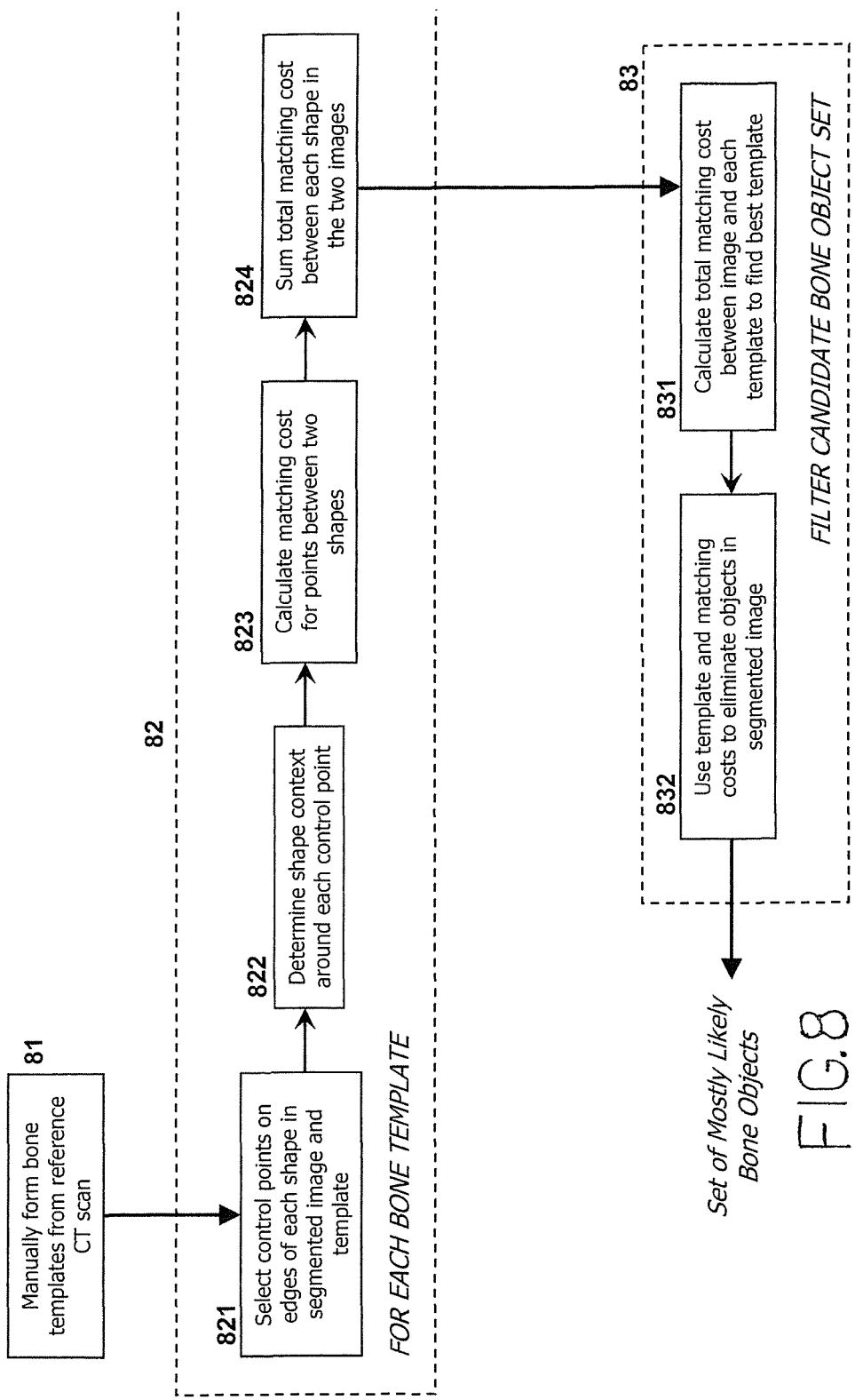
FIG. 8 is a flowchart illustrating the logical process implementing shape matching and object recognition component shown in FIG. 6.

Shape matching and object recognition, as performed in process 63 of FIG. 6, is shown in more detail in FIG. 8. This stage of the system analyzes the set of candidate bone objects and removes those less likely to be actual bone matter via a shape matching approach. The input is the set of candidate bone objects created by initial segmentation stage, represented by a segmented slice image.

At step 81, bone templates are manually formed from reference CT scan. Bone templates are created using CT images from the Visible Human Project, by manually selecting bone regions from the chosen slices. Template matching is necessary since the set of candidate objects created by initial segmentation is likely to contain blood tissue and fluids as well as bone matter, and these must be filtered out.

Then for each bone template, process 82 is performed. In step 821, control points on edges of each shape in segmented image and template are selected. The method for shape matching was introduced by "Shape matching and object recognition using shape contexts" (S. Belongie, J. Malik and J. Puzicha, *IEEE Trans. on Pattern Analysis and Machine Intelligence*, vol. 24, no. 4, pp. 509-522, April 2002). Each bone template $R_i$ is considered in turn. For each object in the segmented image $I_8$ and each object in the bone template $R_i$, control points are placed around the edge. These control points allow matching of objects between the two images. The number of control points used for each object is a percentage of its total number of edge points.

At step 822, the shape context around each control point is determined. Shape context is a way of describing a shape that allows for measuring shape similarity. For a control point $p_i$ on the contour of an object, the shape context is given by:

$$h_i(k) = \text{Card}[q \neq p_i : (q - p_i) \in bin(k)] \quad (15)$$

In other words, shape context is provided by the histogram of the relative coordinates of all the other control points around the same object. We calculate the shape context for all contour points in both the template image and the segmentation image.

At step 823, matching cost for points between two shapes is calculated, and at step 824, the total matching cost between each shape is determined. The cost $C_r$ of matching a point $p_i$ in the segmented image with a point $q_j$ in the bone template is:

$$C_r(p_i, q_j) = \frac{1}{2} \sum_{k=1}^{K} \frac{[h_{ri}(k) - h_{rj}(k)]^2}{h_{ri}(k) + h_{rj}(k)} \quad (16)$$

where $h_{ri}(k)$ and $h_{rj}(k)$ are the shape contexts for the two points. This cost function quantitatively assesses the degree of match between any pair of points on the contours of the two shapes. Each shape in the template image is individually matched with every shape in the segmented image. This is done by calculating the shape contexts for every control point along the contour of the template shape T and the segmented shape $S_i$ currently being considered, then calculating the cost for matching each point from T to a point on $S_i$. The overall cost of a matching T and $S_i$ is the sum of all individual point match costs.

The output of process 82 is input to process 83, filter candidate bone object set. There, at step 831, the total matching cost between segmented image and each bone template is calculated to find best template. The steps in process 82 are repeated for each bone template image. An image match cost value is calculated each time as the sum of the shape match costs between the segmented image and template. The best bone template $R_{r_{opt}}$, for the CT slice currently under consideration is the one that gives the lowest image match cost. Or, more formally:

$$r_{opt} = \arg_{1 \leq i \leq R} \min(C_m(I, R_i)) \quad (17)$$

At step 832, the "best" template is used to eliminate objects in segmented image. We use the template $R_{r_{opt}}$ to select the most likely bone objects from the candidate set. This is done by sequentially eliminating individual candidate bone objects from the segmented image, then calculating the image match cost between the resulting segmentation partition and the bone template. If an object representing bone is incorrectly removed, this cost will increase. Conversely, if a non-bone object is removed, the cost will decrease. This method is repeated to obtain the lowest matching cost; the corresponding segmentation partition contains the most likely set of bone objects.

Figure 9:
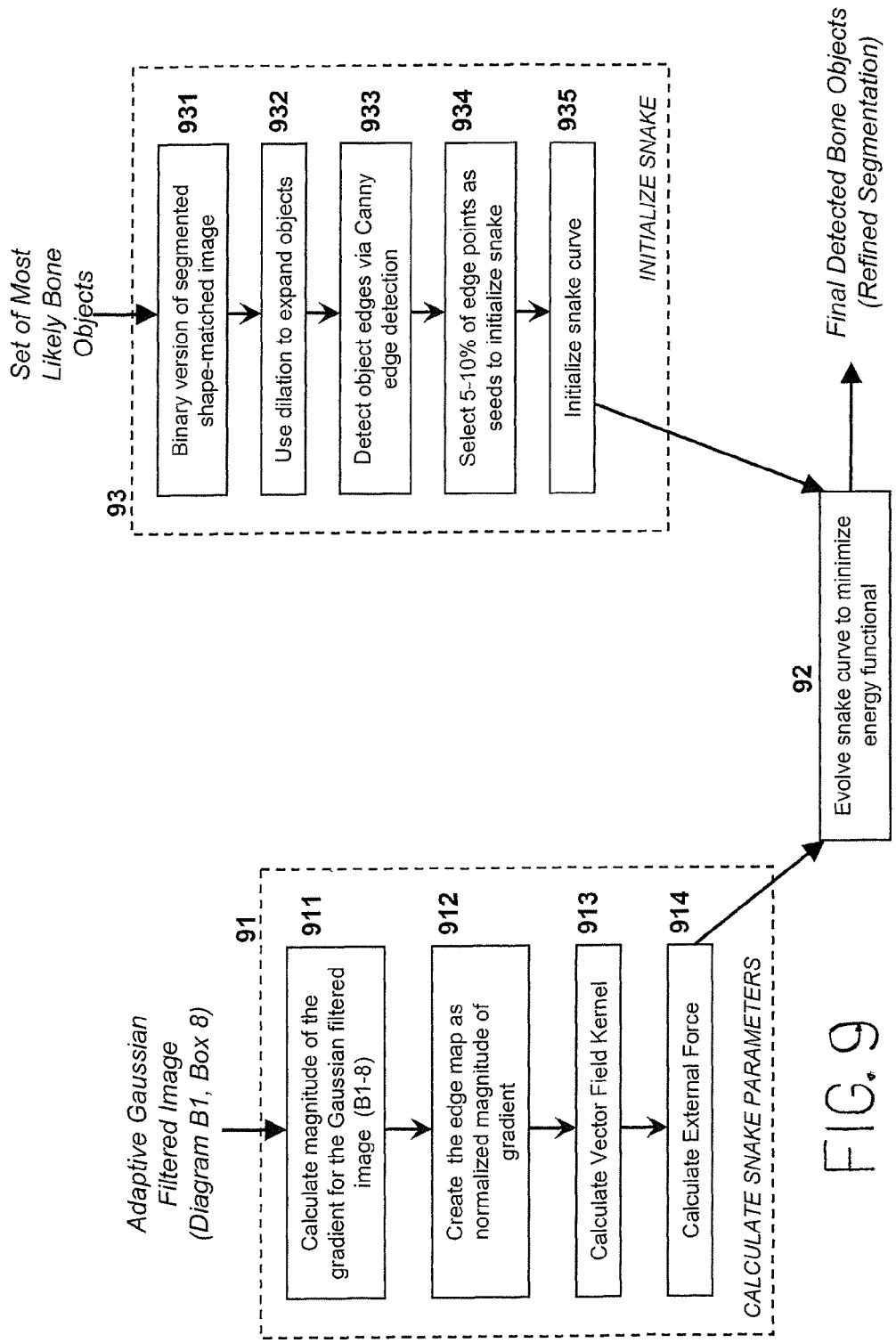
FIG. 9 is a flowchart illustrating the logical process implementing the second CT segmentation component shown in FIG. 6.

The second segmentation stage 66 shown in FIG. 6 is illustrated in more detail in FIG. 9. This stage of the system takes the set of likely bone objects returned by shape matching and performs more accurate segmentation using a snake method. This is the second and final stage of bone detection/segmentation. The input to this stage is the set of most likely bone objects created during object recognition, and the adaptive Gaussian filtered version of the original image created during the initial segmentation stage (see FIG. 7).

The first process 91 is to calculate snake parameters. At step 911, the magnitude of the gradient for the adaptive gaussian filtered version of the original image ($I_5$) is calculated, and in step 912, the edge map is created. Active contours (or snakes) are used frequently in computer vision for detecting object edges. A snake is defined as an energy minimizing spline, whose energy depends on its shape and location within the image. Its behavior is guided by external and internal forces, and use of the right external force helps guide the snake toward edges. For this, we use the Vector Field Convolution (VFC) method, as defined in "Active contour external force using vector field convolution for image segmentation" (Bing Li and Scott T. Acton, *IEEE Trans. on Image Processing*, vol. 16, no. 8, pp. 2096-2106, August 2007). First, the edge map f(x, y) is calculated from the image $I_5$ (generated in the initial segmentation stage by applying an adaptive Gaussian filter to the original abdomen image $I_2$). This is done by calculating $I_5$'s gradient magnitude, using the following formula:

$$|\nabla f| = \sqrt{\left(\frac{\partial f}{\partial x}\right)^2 + \left(\frac{\partial f}{\partial y}\right)^2} \quad (18)$$

where $$\nabla f(x, y) = \frac{\partial f(x, y)}{\partial x} i + \frac{\partial f(x, y)}{\partial y} j \quad (19)$$

The edge map is generated by dividing the gradient magnitude at each point (x, y) in $I_5$ by the maximum magnitude in $I_5$.

At step 913, the Vector Field Kernel (VFK) is calculated. The vector field kernel (VFK) k(x, y)=[$u_k$(x, y), $v_k$(x, y)] is defined by:

$$k(x,y) = m(x,y) n(x,y) \quad (20)$$

where m(x, y) is the magnitude of the vector at (x, y) and n(x, y) is the unit vector that points towards the kernel origin. This is given by:

$$n(x, y) = \left[\frac{-x}{r}, \frac{-y}{r}\right] \quad (21)$$

where r is the Euclidean distance from the origin.

At step 914, VFC external force is calculated using VFK. The external force to apply to the snake is calculated as the convolution of the VFK determined in step 913 and the edge map generated in step 912:

$$f_{vfc}(x,y) = f(x,y) * k(x,y) \quad (22)$$

In the edge map, points near image edges have larger values, so they contribute more to the VFC force. This causes the snake to be attracted to edges in the image, i.e., the contours of bone objects. This force is passed straight to process 92, which evolves the snake.

The input to process 93, initialize snake, is the set of most likely bone objects. In step 931, the binary version of shape-matched image is obtained, and in step 932, dilation is applied to enlarge region's shape. The segmented shape-matched image containing most likely bone objects is thresholded to give a binary image $B_5$. The separate regions, or objects, in the binary image are identified. In the original image, these regions are most likely to contain the pelvic bones. Once identified, morphological dilation is applied to enlarge each region. This ensures that the edges of the regions in $B_5$ are outside the natural bone edges in the segmented shape-matched image.

In step 933, the object edges in shape-matched image are detected via Canny edge detection, and in step 934, 5-10% of edge points are selected as seeds to initialize the snake. Edges in the shape-matched image are identified using Canny edge detection; full mathematical details on this method can be found in "A Computational Approach to Edge Detection" (John Canny, *Readings in Computer Vision*, Fischler and Firschein, Eds., Morgan Kaufmann Pub., pp. 184-203, 1987). Seeds for initializing the snake are then placed along the detected edges at approximately equal distances apart. The total number of seeds placed is 5-10% of total edge length.

In step 935, the snake curve is initialized. More specifically, the snake curve is initialized as a B-spline curve. This is a continuous parametric curve that depends only on a set number of control points, and is defined by:

$$x(u) = \sum_{i=1}^{N} v_i B_i^k(u) \quad (23)$$

where $B_i^k$(u) are the polynomial blending functions, u is the curve parameter, and $v_1, \ldots, v_N$ are the control points. When initializing the snake, the control points are provided by sampling the seed points generated in step 934 at a step of 0.15.

Returning to process 92, the snake curve is evolved to minimize energy functional. The snake curve evolves by trying to minimize the sum of its internal and external energies, defined by the energy functional:

$$E = \int_0^1 \frac{\alpha}{2} |S'(s)|^2 ds + \int_0^1 \frac{\beta}{2} |S''(s)|^2 ds + \int_0^1 F(S) ds \quad (24)$$

F(S) is the external energy, calculated as described above, and is minimal near object edges. α and β are the parameters that control the curve's tension and rigidity, respectively. Full details can be found in: "Snakes: Active contour models" (Michael Kass, Andrew Witkin and Demetri Terzopoulos, *International Journal of Computer Vision*, vol. 1, no. 4, pp. 321-331, January 1988).

Figure 10:
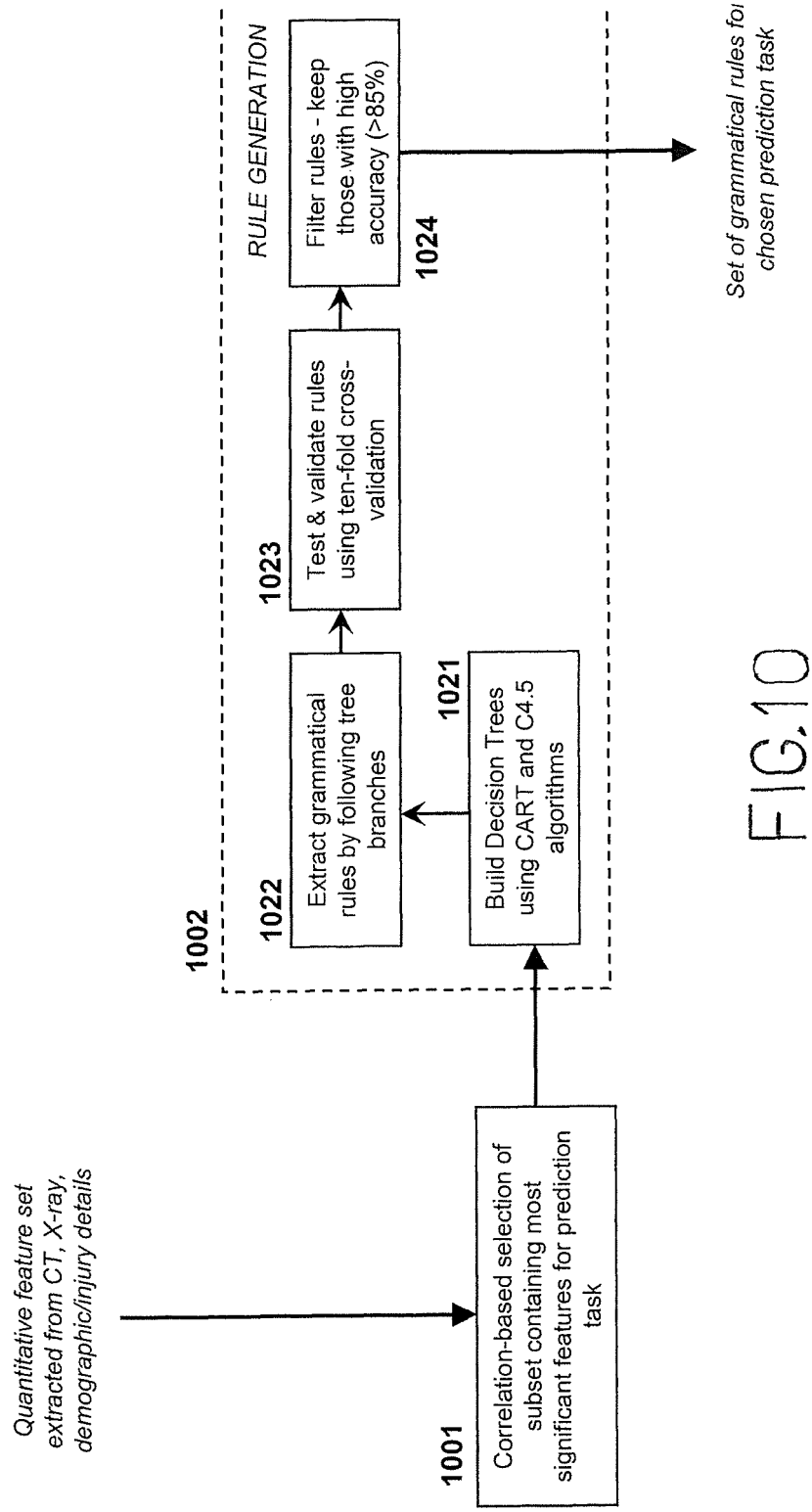
FIG. 10 is a flowchart illustrating the logical process implementing the generation of decision trees and rule extraction of the embodiment shown in FIG. 1.

FIG. 10 illustrates the processes of decision tree generation and rule extraction. This final stage of the system shown in FIG. 1 uses the features extracted in the CT and X-ray processing stages to generate prediction rules for patient outcomes. The input to this stage are features extracted in previous steps (quantitative displacement measures and fracture details). As with the Spline/ASM segmentation stage, this component of the system requires training prior to deployment. Unlike Spline/ASM, this stage can be easily rerun as new cases are added to the labeled patient database, to improve the predictive quality of the generated rules. As previously described with reference to FIG. 1, during the training phase the demographic and injury data input at 12 and stored in database 13 is a prior dataset used to train the predictive model generated by the data processor 14. This prior dataset, along with matching CT and/or X-ray images for each patient and their eventual outcome is used during the training phase to generate predictive models. When the generated model is later used to make predictions for a new patient, the same information is collected and used as input.

In step 1001, a correlation-based selection is made of subset containing most significant features for prediction task. The Correlation-based Feature Selector algorithm (CFS) ranks feature subsets according to a correlation-based evaluation function, favoring those than contain features highly correlated with the class and uncorrelated with each other. This chooses the most predictive feature subset for the task. The evaluation function is given by:

$$M_S = \frac{n \bar{r}_{cf}}{\sqrt{n + n(n-1) \bar{r}_{ff}}} \quad (25)$$

where $M_S$ is the heuristic goodness of a feature subset S containing n features, $\bar{r}_{cf}$ is the mean correlation between features and classes (f∈S) and $\bar{r}_{ff}$ is the average correlation between features. Full implementation details are found in "Correlation-based Feature Selection for Machine Learning" (M. A. Hall, PhD thesis, University of Waikato, Hamilton, New Zealand, 1998).

The results are input to rule generation process 1002. In step 1021, decision trees are built using CART and C4.5 algorithms. Using the reduced feature subset output by process 1001, the Classification and Regression Tree (CART) and C4.5 algorithms are used to build binary decision trees classifying input cases into one of two classes (for example, ICU (Intensive Care Unit) days≦2 and >2). At each step of tree construction, the process chooses the "best" variable to split on, where "best" reflects how well the split creates subsets that have the same value as the target variable.

CART uses the Gini index, which measures the impurity of a data partition. It reaches its maximum value when the two subset sizes at the node are equal, and minimum when only one of the two classes is present at the node. Gini index is defined as:

$$Gini(D) = 1 - \sum_{i=1}^{m} p_i^2 \quad (26)$$

where $p_i$ is the probability that a member of set D belongs to class $C_i$, estimated as $$\frac{|C_{i,D}|}{|D|}.$$

In this embodiment, there are two classes $C_1$ and $C_2$. Full details on CART are provided in *Classification and Regression Trees* (L. Breiman, Chapman & Hall/CRC, 1984).

C4.5 splits on the variable with the highest normalized information gain, a measure based on the concept of entropy. This is calculated as:

$$IG(S,A) = Entropy(S) - Entropy(S|A) \quad (27)$$

where S is the dataset, A is the splitting variable, and entropy is defined as:

$$Entropy(S) = -\sum_{i=1}^{n} p(s_i) \log_2 p(x_i) \quad (28)$$

where p is the probability mass function of S. Full implementation details for C4.5 can be found in *Programs for Machine Learning* (John Ross Quinlan, Morgan Kaufmann Pub., 1993).

In step 1022, grammatical rules are extracted by following tree branches. The decision trees output by step 1021 can be converted to sets of IF-THEN grammatical rules by following each combination of branches down to its leaf node (which contains a class label). The number of rules extracted depends on the size of the tree. Each rule takes the form: IF (combination of attribute values) THEN (class label).

In step 1023, test plus validate rules are applied using ten-fold cross-validation, and in step 1024, filter rules are applied, keeping those with high accuracy (>85%). Filtering is applied to the set of rules output by step 1022. Rules that apply to too few examples in the training set are removed. Accuracy, sensitivity and specificity measures are individually calculated for each of the remaining rules. Rules with >85% accuracy are retained. The performance metrics are calculated using ten-fold cross validation to better test the generalization capabilities of each rule.

Figure 11:
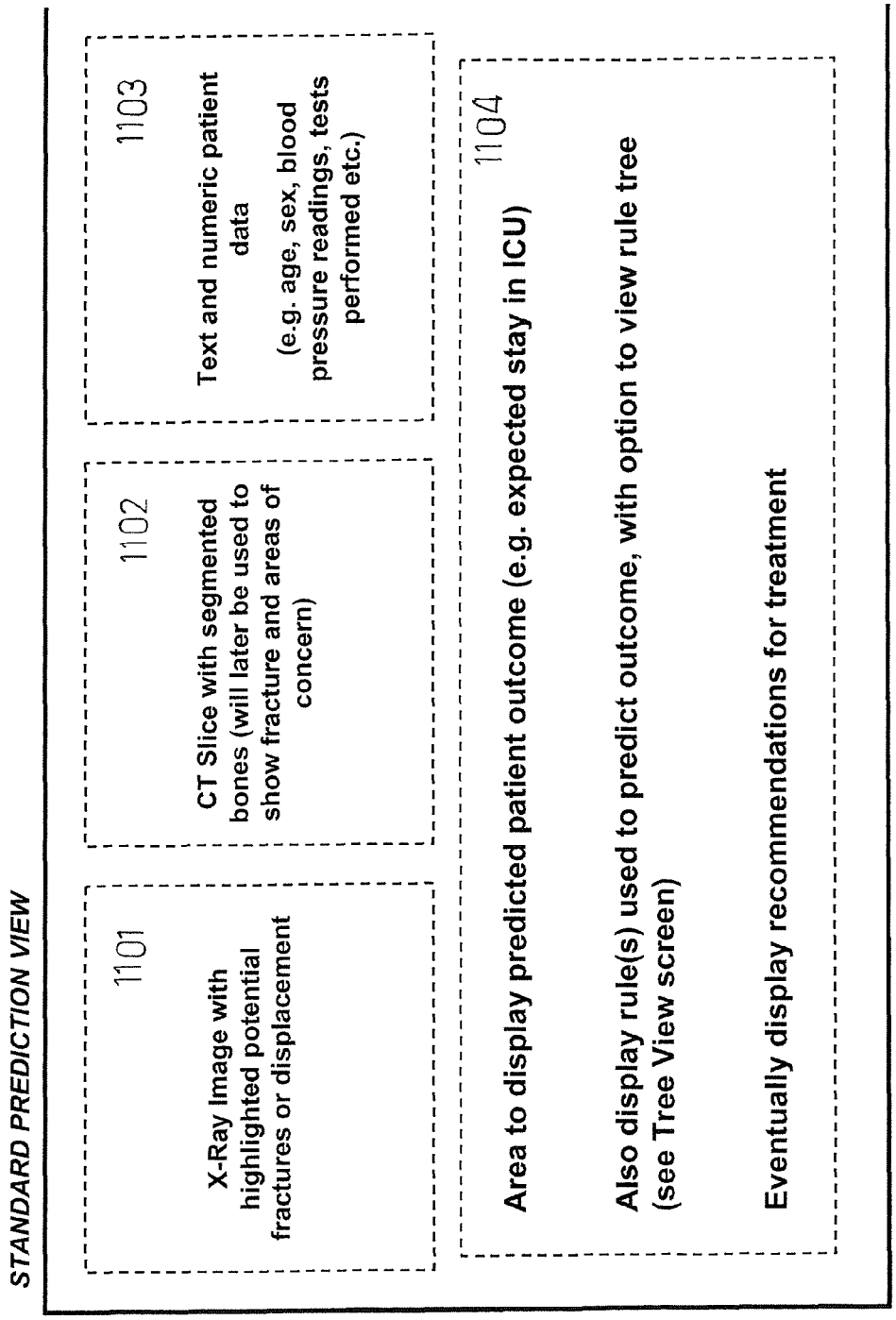
FIG. 11 is a diagrammatic view representing a standard prediction view displayed on the screen of the display 15 shown in FIG. 1.
Figure 12:
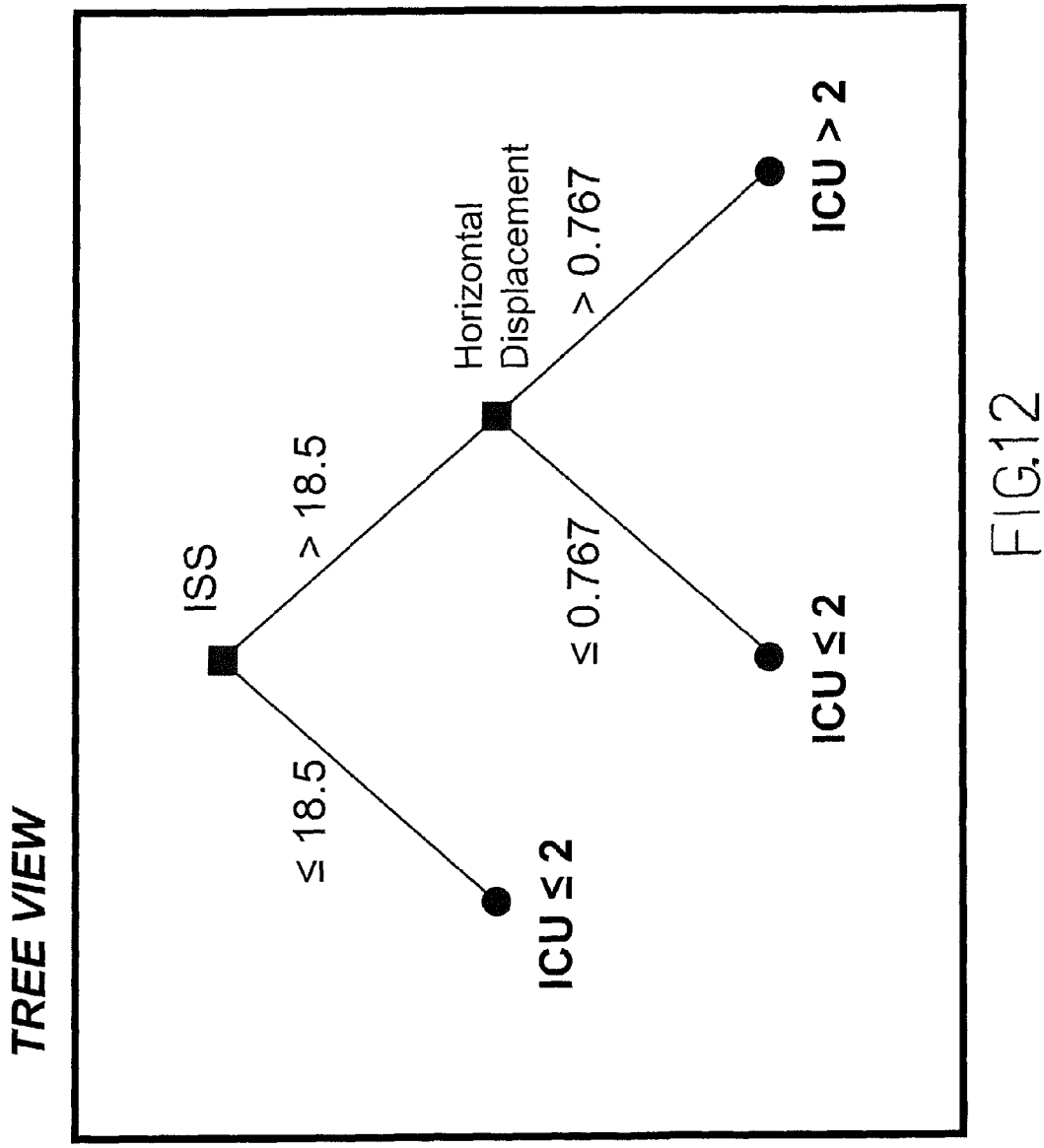
FIG. 12 is a diagrammatic view representing a tree view displayed on the screen of the display 15 shown in FIG. 1.

As described with reference to FIG. 1, the decision support system of the embodiment of the invention provides views on display 15 which advise and assist the physician in treatment of the patient. FIG. 11 illustrates in diagrammatic form a standard prediction view. The display screen is divided into four areas, three across the top of the display screen and one across the bottom of the screen. It will be understood, however, that this arrangement and contents can be varied within the scope of the invention. In the example illustrated, the first area 1101 provides a display of the X-ray image with highlighted potential fractures or displacement. The next area 1102 provides a display of a CT slice with segmented bones which will be used to show fracture and areas of concern. The third area 1103 provides text and numeric patient data, such as age, sex, blood pressure readings, tests performed, and other pertinent data. The area 1104 below the first three areas provides predicted patient outcome (e.g., expected stay in Intensive Care Unit), the rules used to predict patient outcome, with option to view rule tree, and recommendations for treatment. Should the physician elect to view the rule tree, the tree view shown in FIG. 12 would be presented on display 15 shown in FIG. 1.

While the invention has been described in teens of a single preferred embodiment, those skilled in the art will recognize that the invention can be practiced with modification within the spirit and scope of the appended claims.

The invention claimed is:

1. An automated decision-support system for analysis of bone X-ray and computed tomography (CT) images to provide diagnostic and therapeutic recommendations, comprising:
    means for inputting X-ray bone images;
    first pre-processing means for automated segmenting of multiple bone X-ray image structures, said automated segmenting being performed on each structure individually using Active Shape Model (ASM) technique, a previously detected bone structure being used to begin detection of a next bone structure;
    fracture detection means receiving segmented multiple bone X-ray images from said first pre-processing means and outputting data identifying one or more detected fractures in an X-ray bone image;
    displacement calculation means receiving segmented multiple bone X-ray images from said pre-processing means and measuring displacements of bone segments;
    means for inputting CT bone images;
    second pre-processing means for automated segmenting of multiple bone CT image structures,
    template/shape matching means receiving segmented multiple bone CT images from said second pre-processing means and identifying segmented bone images;
    a processed trauma database receiving and storing data from said fracture detection means, said displacement calculation means, and said template/shape matching means;
    data processor means for accessing data in said processed trauma database, applying machine learning to accessed data, and generating rules for predicting injury severity;
    display means coupled with user interface means for receiving and displaying diagnostic information including images of detected bone fractures and predictions of injury severity from said data processor means, said user interface configured to receive user input of therapy to be administered to a patient; and
    a patient record database recording the diagnostic information and therapy to be administered for the patient.

2. The automated decision-support system according to claim 1, wherein the ASM technique of said first pre-processing means incorporates cubic spline interpolation to regulate shape curvature of segmented X-ray bone images.

3. The automated decision-support system according to claim 2, wherein the ASM technique of said first pre-processing means uses landmark positions to calculate symmetry and horizontal/vertical gap measures of segmented X-ray bone images.

4. The automated decision-support system according to claim 1, wherein fracture detection means detects possible fractures in X-ray bone images using wavelet transform and edge tracing techniques.

5. The automated decision-support system according to claim 1, wherein said second pre-processing means uses bone masks and seed growing techniques to extract objects potentially representing bone in a CT slice.

6. The automated decision-support system according to claim 5, wherein said second pre-processing means uses bone masks in combination with shape matching to identify candidate bone objects.

7. The automated decision-support system according to claim 5, wherein said second pre-processing means uses automated seeding of a Snake Model and uses the Snake Model to improve segmentation of bones.

8. The automated decision-support system according to claim 1, further including means for inputting other information, including demographics and injury details, to said processed trauma database, said data processing means accessing said other information for generating rules for predicting injury severity and recommended therapy.

9. The automated decision-support system according to claim 8, wherein the means for inputting other information inputs prior patient datasets to train a predictive model using machine learning by said data processor means, said data processor means using the predictive model to make predictions for a new patient.

10. The automated decision-support system according to claim 1, wherein the X-ray bone images and the CT bone images are of a patient's pelvic region.

11. The automated decision-support system according to claim 1, wherein the display means displays an X-ray image with highlighted potential fractures or displacements, a CT slice image with segmented bones showing fracture and areas of concern, patient data, and predicted patient outcome and recommendations for treatment.

12. The automated decision-support system according to claim 11, wherein the display means further displays rules used to predict patient outcome with an option to view a rule tree, the display means displaying a rule tree when the option to do so is selected via the user interface means.

13. An automated decision-support method performed by a computer for analysis of bone X-ray and computed tomography (CT) images to provide diagnostic and therapeutic recommendations, comprising the steps of:

inputting X-ray bone images;
automated segmenting of multiple bone X-ray image structures, said automated segmenting being performed on each structure individually using Active Shape Model (ASM) technique, a previously detected bone structure being used to begin detection of a next bone structure;
receiving segmented multiple bone X-ray images and outputting data identifying one or more detected fractures in an X-ray bone image;
calculating displacement of received segmented multiple bone X-ray images from and measuring displacements of bone segments;
inputting CT bone images;
automated segmenting of multiple bone CT image structures,
receiving segmented multiple bone CT images and identifying segmented bone images using template/shape matching;
receiving and storing data of detected fractures, calculated displacement, and identified segmented bone CT images in a processed trauma database;
accessing data in said processed trauma database, applying machine learning to accessed data, and generating rules for predicting injury severity;
receiving and displaying diagnostic information including images of detected bone fractures and predictions of injury severity;
receiving user input of therapy to be administered to a patient; and
storing diagnostic information and therapy to be administered for the patient in a patient record database.

14. The automated decision-support method according to claim 13, wherein the ASM technique incorporates cubic spline interpolation to regulate shape curvature of segmented X-ray bone images.

15. The automated decision-support method according to claim 14, wherein the ASM technique uses landmark positions to calculate symmetry and horizontal/vertical gap measures of segmented X-ray bone images.

16. The automated decision-support method according to claim 13, wherein detection of possible fractures in X-ray bone images is performed using wavelet transform and edge tracing techniques.

17. The automated decision-support method according to claim 13, wherein bone masks and seed growing techniques are used to extract objects potentially representing bone in a CT slice.

18. The automated decision-support method according to claim 17, wherein bone masks in combination with shape matching is used to identify candidate bone objects.

19. The automated decision-support method according to claim 17 wherein automated seeding of a Snake Model is performed and the Snake Model is used to improve segmentation of bones.

20. The automated decision-support method according to claim 13, further including the step of inputting other information, including demographics and injury details, to said processed trauma database, said other information being accessed for generating rules for predicting injury severity and recommended therapy.

21. The automated decision-support method according to claim 20, wherein the step of inputting other information inputs prior patient datasets to train a predictive model using machine learning by computer, said computer using the predictive model to make predictions for a new patient.

22. The automated decision-support method according to claim 13, wherein the X-ray bone images and the CT bone images are of a patient's pelvic region.

23. The automated decision-support method according to claim 13, wherein the step of receiving and displaying includes displaying an X-ray image with highlighted potential fractures or displacements, a CT slice image with segmented bones showing fracture and areas of concern, patient data, and predicted patient outcome and recommendations for treatment.

24. The automated decision-support method according to claim 23, wherein the step of receiving and displaying further includes displaying rules used to predict patient outcome with an option to view a rule tree, and displaying a rule tree when the option to do so is selected via a user interface.

25. An automated decision-support system for analysis of bone X-ray images to provide diagnostic and therapeutic recommendations, comprising:

means for inputting X-ray bone images;

pre-processing means for automated segmenting of multiple bone X-ray image structures, said automated segmenting being performed on each structure individually using Active Shape Model (ASM) technique, a previously detected bone structure being used to begin detection of a next bone structure;

fracture detection means receiving segmented multiple bone X-ray images from said first pre-processing means and outputting data identifying one or more detected fractures in an X-ray bone image;

displacement calculation means receiving segmented multiple bone X-ray images from said pre-processing means and measuring displacements of bone segments;

means for inputting other information, including demographics and injury details, to said processed trauma database, said data processing means accessing said other information for generating rules for predicting injury severity and recommended therapy;

a processed trauma database receiving and storing data from said fracture detection means and said displacement calculation means;

data processor means for accessing data in said processed trauma database, applying machine learning to accessed data, and generating rules for predicting injury severity, said means for inputting other information receiving prior patient datasets to train a predictive model using machine learning by said data processor means, said data processor means using the predictive model to make predictions for a new patient;

display means coupled with user interface means for receiving and displaying diagnostic information including images of detected bone fractures and predictions of injury severity from said data processor means, said user interface configured to receive user input of therapy to be administered to a patient; and a patient record database recording the diagnostic information and therapy to be administered for the patient.

* * * * *

UNITED STATES PATENT AND TRADEMARK OFFICE
CERTIFICATE OF CORRECTION

| | | |
|---|---|---|
| PATENT NO. | : 8,538,117 B2 | Page 1 of 1 |
| APPLICATION NO. | : 13/255542 | |
| DATED | : September 17, 2013 | |
| INVENTOR(S) | : Najarian et al. | |

It is certified that error appears in the above-identified patent and that said Letters Patent is hereby corrected as shown below:

Specification

At column 1, line 14, please delete the entire paragraph and insert the following:

--This invention was made with government support under contract number IIS0758410 awarded by the National Science Foundation. The government has certain rights in the invention.--.

Signed and Sealed this
Third Day of November, 2015

Michelle K. Lee
*Director of the United States Patent and Trademark Office*